US010235902B2

(12) United States Patent
Schulhofer et al.

(10) Patent No.: US 10,235,902 B2
(45) Date of Patent: *Mar. 19, 2019

(54) CALORIE OPTIMIZATION RESPIRATORY EXCHANGE (CORE) METABOLIC PROFILE SYSTEM AND METHOD

(71) Applicant: Core Metabolics LLC, Santa Fe, NM (US)

(72) Inventors: Sanford David Schulhofer, Santa Fe, NM (US); Benjamin Stone, Vail, CO (US)

(73) Assignee: CORE METABOLICS LLC, Santa Fe, NM (US)

( * ) Notice: Subject to any disclaimer, the term of this patent is extended or adjusted under 35 U.S.C. 154(b) by 138 days.

This patent is subject to a terminal disclaimer.

(21) Appl. No.: 15/189,704

(22) Filed: Jun. 22, 2016

(65) Prior Publication Data
US 2016/0379521 A1 Dec. 29, 2016

Related U.S. Application Data

(60) Provisional application No. 62/184,766, filed on Jun. 25, 2015.

(51) Int. Cl.
*A63F 9/24* (2006.01)
*G09B 19/00* (2006.01)
(Continued)

(52) U.S. Cl.
CPC ......... *G09B 19/0092* (2013.01); *A61B 5/024* (2013.01); *A61B 5/4866* (2013.01); *A61B 5/083* (2013.01); *A61B 2562/0219* (2013.01)

(58) Field of Classification Search
CPC .................................................. G09B 19/0092
See application file for complete search history.

(56) References Cited

U.S. PATENT DOCUMENTS 4,909,259 A * 3/1990 Tehrani .................. A61B 5/083
600/483
6,475,158 B1 * 11/2002 Orr ........................ A61B 5/024
600/529
(Continued)

*Primary Examiner* — Steve Rowland
(74) *Attorney, Agent, or Firm* — McGuire Woods LLP

(57) ABSTRACT

The disclosed embodiments include a calorie optimization respiratory exchange metabolic system comprising a computer-readable storage media having stored thereon computer-executable instructions; a processor for executing the computer-executable instructions, wherein the computer-executable instructions include instructions for receiving user profile data of a user, wherein the user profile data includes age, height, weight, diet, and fitness information; determining five metabolic points versus heart rate; generating an individualized metabolic profile for the user based on the five metabolic points; determining for the user an individualized nutritional guideline from the metabolic profile, wherein the individualized nutritional guideline is determined by percent fat, percent protein and percent carbohydrate to optimize fat metabolism for weight loss, maintenance, and endurance exercise enhancement; and determining an individualized exercise heart rate profile as a percentage of maximum heart rate from the metabolic profile.

11 Claims, 10 Drawing Sheets

(51) Int. Cl.
*A61B 5/024* (2006.01)
*A61B 5/00* (2006.01)
*A61B 5/083* (2006.01)

(56) References Cited

U.S. PATENT DOCUMENTS

| | | | | |
|---|---|---|---|---|
| 2006/0031102 | A1* | 2/2006 | Teller | A61B 5/411 |
| | | | | 705/3 |
| 2006/0228681 | A1* | 10/2006 | Clarke | A63B 24/00 |
| | | | | 434/236 |
| 2006/0264730 | A1* | 11/2006 | Stivoric | A61B 5/0205 |
| | | | | 600/390 |
| 2007/0282176 | A1* | 12/2007 | Shimada | G16H 40/63 |
| | | | | 600/300 |
| 2014/0087336 | A1* | 3/2014 | Wang | A61B 5/024 |
| | | | | 434/127 |
| 2014/0213920 | A1* | 7/2014 | Lee | A61B 5/222 |
| | | | | 600/509 |
| 2014/0249379 | A1* | 9/2014 | Proud | H04W 4/70 |
| | | | | 600/301 |
| 2014/0330094 | A1* | 11/2014 | Pacione | A61B 5/411 |
| | | | | 600/301 |

* cited by examiner

FIGURE 2

 My Cardiovascular Exercise

 I get little to no exercise.

 I participate in intensive exercise for at least 20 minutes 1 to 3 times per week. (This may include such things as bicycling, jogging, basketball, swimming, skating, etc. If you do not exercise regularly, but you maintain a busy life style that requires you to walk frequently for longer periods, you meet the requirements of this level.)

 I participate in intensive exercise for at least 30 to 60 minutes to 3 to 4 times per week. Any of the activities listed above will qualify.

 I participate in intensive exercise for at least 60 minutes or greater 5 to 7 days per week. (Any of the activities listed above will qualify. Labor-intensive occupations such as construction work (brick laying, carpentry, general labor, etc.), farming, landscape worker or similar occupation will qualify.

 I participate in exceedingly active and/or very demanding activities. Examples include: (1) athlete with an almost unstoppable training schedule with multiple training sessions throughout the day (2) very demanding job, such as shoveling coal or working long hours on an assembly line. Generally, this level of activity is very difficult to achieve.

| 18 | My Daily Fat (%)<br>*If you do not know your average daily fat intake, then we suggest using the default of 18%. This number can be adjusted later.* |
|---|---|
| 45 | My Resting Heart Rate<br>Enter your heart rate when you just get up in the morning or when you are sitting quietly. If you do not know your resting heart rate, then we suggest using the default value of 65. This number may be adjusted later. |

FIGURE 3

| | AGE | | | |
|---|---|---|---|---|
| % Heart Rate (Carb) | % Heart Rate (Peak) | Kcal/min EDL | Kcal/min Peak | VALUE |
| 70 | 50 | 2.1 | 3.4 | 26 |
| 70 | 50 | 2.1 | 3.4 | 27 |
| 69 | 50 | 2.1 | 3.4 | 28 |
| 69 | 50 | 2.1 | 3.4 | 29 |
| 68 | 50 | 2.1 | 3.4 | 30 |
| 68 | 50 | 2.1 | 3.4 | 31 |
| 67 | 50 | 2.1 | 3.4 | 32 |
| 67 | 50 | 2.1 | 3.4 | 33 |
| 66 | 50 | 2.1 | 3.4 | 34 |
| 66 | 56 | 3.2 | 3.7 | 35 |
| 65 | 56 | 3.2 | 3.7 | 36 |
| 65 | 56 | 3.2 | 3.7 | 37 |
| 64 | 56 | 3.2 | 3.7 | 38 |
| 64 | 56 | 3.2 | 3.7 | 39 |
| 64 | 56 | 3.2 | 3.7 | 40 |
| 64 | 56 | 3.2 | 3.7 | 41 |
| 69 | 60 | 3.5 | 3.9 | 42 |
| 69 | 60 | 3.5 | 3.9 | 43 |
| 69 | 60 | 3.5 | 3.9 | 44 |
| 69 | 60 | 3.5 | 3.9 | 45 |
| 69 | 60 | 3.5 | 3.9 | 46 |
| 69 | 60 | 3.5 | 3.9 | 47 |
| 69 | 60 | 3.5 | 3.9 | 48 |
| 69 | 60 | 3.5 | 3.9 | 49 |
| 69 | 60 | 3.5 | 3.9 | 50 |
| 68 | 53 | 2.8 | 3.4 | 51 |
| 68 | 53 | 2.8 | 3.4 | 52 |
| 68 | 53 | 2.8 | 3.4 | 53 |
| 68 | 53 | 2.8 | 3.4 | 54 |
| 68 | 53 | 2.8 | 3.4 | 55 |
| 67 | 52 | 1.8 | 2.9 | 56 |
| 67 | 52 | 1.8 | 2.9 | 57 |
| 67 | 52 | 1.8 | 2.9 | 58 |
| 67 | 52 | 1.8 | 2.9 | 59 |
| 67 | 52 | 1.8 | 2.9 | 60 |

FIGURE 4

| NUTRITION (% FAT IN DIET) | | | | |
|---|---|---|---|---|
| % Heart Rate (Carb) | % Heart Rate (Peak) | Kcal/min EDL | Kcal/min Peak | VALUE |
| NULL | NULL | 0.1 | 3.5 | 10 |
| NULL | NULL | 0.1 | 3.5 | 11 |
| NULL | NULL | 0.1 | 3.5 | 12 |
| NULL | NULL | 0.1 | 3.5 | 13 |
| NULL | NULL | 0.8 | 3.5 | 14 |
| NULL | NULL | 0.8 | 3.9 | 15 |
| NULL | NULL | 0.8 | 3.9 | 16 |
| NULL | NULL | 1.6 | 3.9 | 17 |
| NULL | NULL | 1.6 | 3.9 | 18 |
| NULL | NULL | 1.6 | 3.9 | 19 |
| NULL | NULL | 1.6 | 4.1 | 20 |
| NULL | NULL | 2.5 | 4.1 | 21 |
| NULL | NULL | 2.5 | 4.1 | 22 |
| NULL | NULL | 2.5 | 4.1 | 23 |
| NULL | NULL | 2.5 | 4.1 | 24 |
| NULL | NULL | 2.5 | 4.1 | 25 |
| NULL | NULL | 3.4 | 4.3 | 26 |
| NULL | NULL | 3.4 | 4.3 | 27 |
| NULL | NULL | 3.4 | 4.3 | 28 |
| NULL | NULL | 3.4 | 4.3 | 29 |
| NULL | NULL | 3.9 | 4.3 | 30 |
| NULL | NULL | 3.9 | 4.5 | 31 |
| NULL | NULL | 3.9 | 4.5 | 32 |
| NULL | NULL | 3.9 | 4.5 | 33 |
| NULL | NULL | 4.2 | 4.5 | 34 |
| NULL | NULL | 4.2 | 4.5 | 45 |
| NULL | NULL | 4.2 | 4.9 | 36 |
| NULL | NULL | 4.2 | 4.9 | 37 |
| NULL | NULL | 4.6 | 4.9 | 38 |
| NULL | NULL | 4.6 | 4.9 | 39 |
| NULL | NULL | 4.6 | 4.9 | 40 |

FIGURE 5

| EXERCISE INTENSITY (SCALE 1-10) | | | | |
|---|---|---|---|---|
| % Heart Rate (Carb) | % Heart Rate (Peak) | Kcal/min EDL | Kcal/min Peak | VALUE |
| 70 | 68 | 3.9 | 4.4 | 1 |
| 69 | 66 | 3.8 | 4.3 | 2 |
| 68 | 66 | 3.8 | 4.2 | 3 |
| 67 | 67 | 3.7 | 4.1 | 4 |
| 65 | 63 | 3.6 | 4.1 | 5 |
| 64 | 63 | 3.5 | 3.9 | 6 |
| 64 | 63 | 3.4 | 3.8 | 7 |
| 64 | 60 | 3.3 | 3.7 | 8 |
| 63 | 55 | 3.2 | 3.6 | 9 |
| 60 | 55 | 3.1 | 3.6 | 10 |

FIGURE 6

| EXERCISE VOLUME (SCALE 1-5) | | | | |
|---|---|---|---|---|
| % Heart Rate (Carb) | % Heart Rate (Peak) | Kcal/min EDL | Kcal/min Peak | VALUE |
| 65 | 60 | 2.2 | 3.2 | 1 |
| 70 | 64 | 2.4 | 3.5 | 2 |
| 74 | 66 | 2.5 | 3.7 | 3 |
| 77 | 67 | 2.6 | 4.1 | 4 |
| 84 | 70 | 3.1 | 4.5 | 5 |
| | | | | |

FIGURE 7

| PEAK FAT TO MACRONUTRIENT PROFILE | | | | |
|---|---|---|---|---|
| %FAT | %CARB | %PROT | PEAK FAT USE (LOW TO HI) | |
| 30 | 40 | 30 | 0.0 | 0.5 |
| 32 | 40 | 28 | 0.6 | 1.0 |
| 34 | 40 | 26 | 1.1 | 1.5 |
| 34 | 40 | 26 | 1.6 | 2.0 |
| 36 | 40 | 24 | 2.1 | 2.5 |
| 36 | 38 | 26 | 2.6 | 3.0 |
| 38 | 36 | 26 | 3.1 | 3.5 |
| 40 | 34 | 28 | 3.6 | 4.0 |
| 40 | 32 | 30 | 4.1 | 4.5 |
| 40 | 30 | 30 | 4.6 | 5.0 |
| 40 | 30 | 30 | 5.0 | 6.0 |

FIGURE 9

NUTRITIONAL REQUIRMENTS FOR DIETARY PRESCRIPTION

BREAKFAST - A1 — Eggs and toast with butter/quiche/breakfast sandwich containing eggs, other meats, and croissant/bagel
LUNCH - A2 — Some kind of a sandwich containing turkey, chicken, roast beef. I usually put spinach or kale in it with an oily dressing
DINNER - A3 — I usually eat fish, chicken, or beef with a vegetable side, usually steamed or grilled
SNACKS - A4 — I mostly eat nuts, nut butters, and fruits. I very rarely ever eat any kind of candy or potato chips BREAKFAST - B1 — Cereal, granola, or oatmeal (porridge oats)/ Fruit and yogurt parfait with orange, apple, or some other fruit juice
LUNCH - B2 — I do my best to prepare foods for work and the rest of my daily activities, but I usually have some sort of a "health" fast food sandwich.
DINNER - B3 — I like pizza, pasta-based dishes with chicken, turkey, or some kind of fish.
SNACKS - B4 — I snack on low-fat yogurt with nuts, almonds, and sometimes granola bars BREAKFAST - C1 — I usully skip breakfast but sometimes I'll have coffee and a granola bar or donut and possibly a croissant or bagel.
LUNCH - C2 — I can usually put together a sandwich at home containing some kind of poultry based lunch meat with mayo or mustard
DINNER - C3 — I sometimes eat a burger for dinner with fries and possibly a cola drink
SNACKS - C4 — I enjoy snack bars, potato chips, pita chips, and the occasional handful of nut-based candy

| MEAL | CARB | FAT | PROT | CONTRIBUTIONS | |
|---|---|---|---|---|---|
| Breakfast | | | | Breakfast | 20.00% |
| A1 | 15 | 60 | 25 | Lunch | 27.50% |
| B1 | 55 | 35 | 10 | Dinner | 32.50% |
| C1 | 78 | 5 | 17 | Snack | 20.50% |
| Lunch | | | | | |
| A2 | 30 | 50 | 20 | | |
| B2 | 65 | 15 | 20 | | |
| C2 | 40 | 30 | 30 | | |
| Dinner | | | | | |
| A3 | 20 | 45 | 35 | | |
| B3 | 43 | 32 | 25 | | |
| C3 | 55 | 30 | 15 | | |
| Snack | | | | | |
| A4 | 30 | 50 | 20 | | |
| B4 | 63 | 17 | 20 | | |
| C4 | 85 | 10 | 5 | | |

(20% breakfast fat %value)+(27

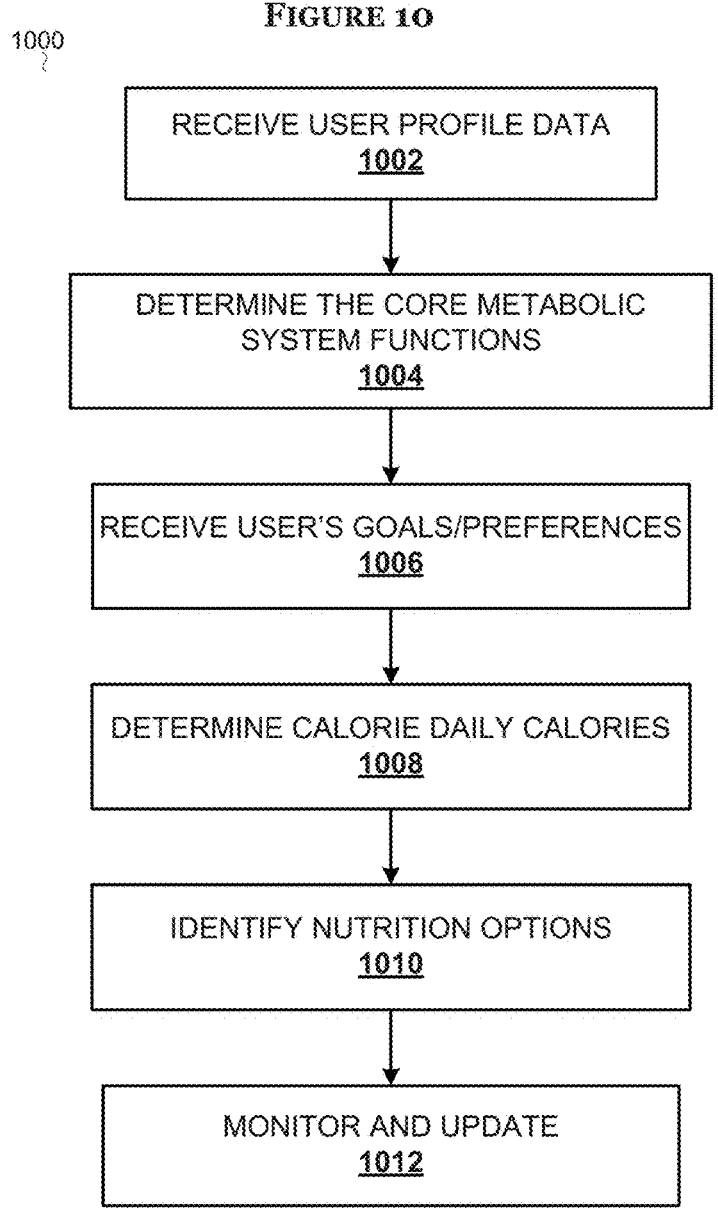

CALORIE OPTIMIZATION RESPIRATORY EXCHANGE (CORE) METABOLIC PROFILE SYSTEM AND METHOD

CROSS-REFERENCE TO RELATED APPLICATION

This application claims priority to U.S. Provisional Patent Application Ser. No. 62/184,766, filed Jun. 25, 2015, entitled Calorie Optimization Respiratory Exchange (Core) Metabolic Calculator, the entire teachings of which are incorporated herein.

BACKGROUND

Commonly referred to as VO2 max testing, respiratory exchange measurement requires a skilled technician, a steady-state exercise environment (treadmill or stationary bicycle), a heart rate monitor, a sealed ventilation mask for the collection of respiratory oxygen (O2) and carbon dioxide (CO2) gases associated with inhalation and exhalation, collection hardware with O2 and CO2 sensors, and a computer with specialized software for the accumulation, interpretation and presentation of the collected data. Measurement of O2/CO2 values allows for the determination of metabolism and is the sine qua non for the accurate quantification of the amount of fat or carbohydrate consumed at specific heart rates from rest through anaerobic efforts. This information is used to understand an individual's metabolic profile and is a valuable and critical tool in many medical, nutrition and exercise settings. Given the technical skills, extensive equipment, and facility requirements, there is a paucity of testing centers and a high fee associated with the administration of respiratory exchange tests. Collectively, these factors represent a significant barrier to the widespread use of respiratory exchange testing, despite the overwhelming need throughout the general population. Specifically, respiratory exchange testing is critical to nutrition and diet planning, and an invaluable tool for weight loss and nutrition maintenance.

SUMMARY OF THE INVENTION

Disclosed herein are several embodiments of a novel calorie optimization respiratory exchange (CORE) metabolic profile system and method. The disclosed system and method provide an alternative, yet functionally equivalent outcome, to respiratory exchange testing in a cost-effective and affordable manner with horizontal and vertical scalability to the general population for nutrition, exercise and diet planning.

In one embodiment, the CORE system and method are designed to run in the background of a website or mobile app, thereby allowing a user to enter their biometric data into the CORE system for the determination of their individual metabolic profile and the establishment of their nutritional, fitness and diet plan needs. In certain embodiments, the CORE system may be configured to automatically receive the biometric data of a user from one or more biometric devices such as, but not limited to, a heart rate monitor, a heart rate enabled device, and/or an accelerometer enabled device. These devices may wearable (e.g., smartwatch or Fitbit™), mobile (e.g., a smartphone with an integrated accelerometer and/or hear rate monitor), or stationary.

In addition, in certain embodiments, the CORE system is configured to allow a user to enter data collected directly from respiratory exchange testing that they may have previously performed. The profile may be associated with a wearable heart rate or accelerometer-enabled wearable device for the conversion of estimated kilocalorie expense into fat and carbohydrate kilocalorie expense based upon the user's metabolic profile. In some embodiments, the system is also utilized in conjunction with a calorie restriction equation and energy expenditure estimations to assist the user in designing and implementing weight loss, maintenance, and exercise programs.

An example embodiment disclosed herein include a system comprising a computer-readable storage media having stored thereon computer-executable instructions; a processor for executing the computer-executable instructions, wherein the computer-executable instructions include instructions for: receiving user profile data of a user; determining metabolic points (kcals/min) versus heart rate (beats/minute); generating an individualized metabolic profile for the user; and determining an individualized exercise heart rate profile as a percentage of maximum heart rate from the metabolic profile.

Another example embodiment disclosed herein include a system comprising a computer-readable storage media having stored thereon computer-executable instructions; a processor for executing the computer-executable instructions, wherein the computer-executable instructions include instructions for: receiving user profile data of a user, wherein the user profile data includes age, height, weight, diet, and fitness information; and optionally five metabolic points from personal respiratory exchange test, determining the five metabolic points (kcals/min) versus heart rate (beats/minute) if the five metabolic points from the personal respiratory exchange test; generating an individualized metabolic profile for the user; determining an individualized exercise heart rate profile as a percentage of maximum heart rate from the metabolic profile; and determining for the user an individualized nutritional guideline by percent fat, percent protein and percent carbohydrate to optimize fat metabolism for weight loss, maintenance, and endurance exercise enhancement from the metabolic profile.

Additional embodiments, advantages, and novel features are set forth in the detailed description.

BRIEF DESCRIPTION OF THE DRAWINGS

Illustrative embodiments of the present invention are described in detail below with reference to the attached drawing figures, which are incorporated by reference herein and wherein:

FIG. 2 is an example illustrations of the user queries for fitness and nutrition in accordance with an embodiment;

FIGS. 3-7 illustrate examples of calculated biometrics and data in accordance with an embodiment;

FIG. 9 is an example of a diet plan for meeting a determined individualized nutritional guidelines in accordance with one embodiment; and FIG. 10 illustrates an example algorithm or process executed by the calorie optimization respiratory exchange metabolic system in accordance with one embodiment The illustrated figures are only exemplary and are not intended to assert or imply any limitation with regard to the environment, architecture, design, or process in which different embodiments may be implemented.

DETAILED DESCRIPTION OF THE DRAWINGS

Figure 1:
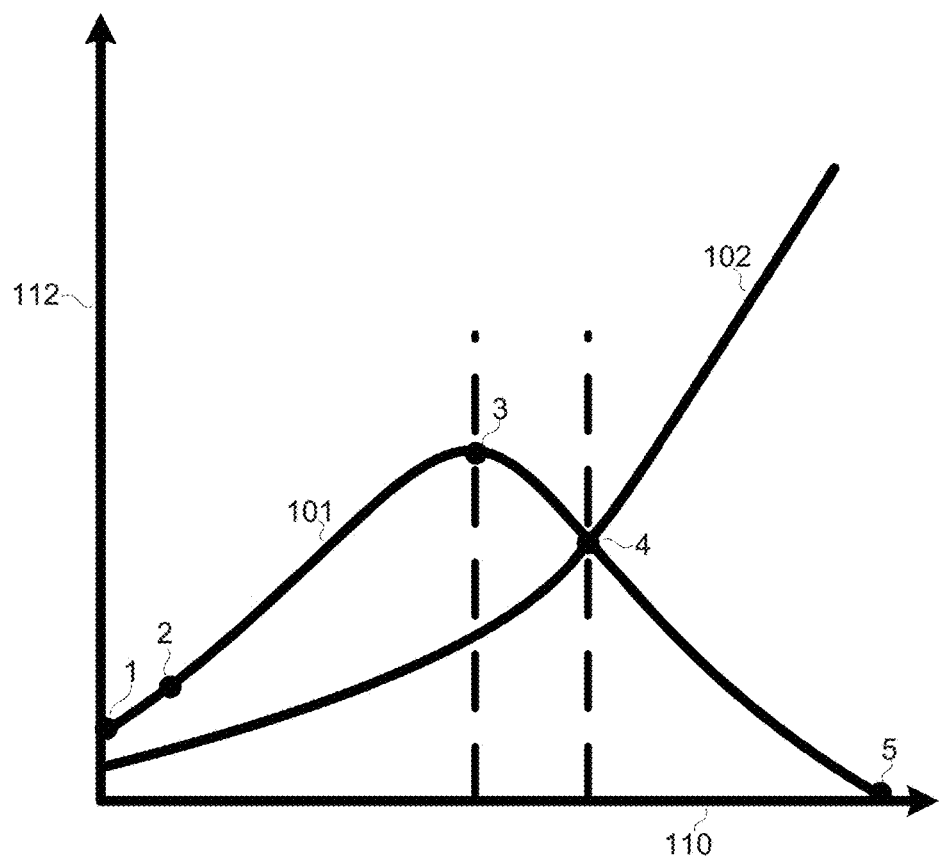
FIG. 1 is a graph depicting substrate utilization (kcal/min vs. heart rate), corresponding to five critical points associated with fat and carbohydrate metabolism in accordance with an embodiment.

The invention and the various features and advantageous details thereof are explained more fully with reference to the non-limiting embodiments that are illustrated in the accompanying drawings and detailed in the following description. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, descriptions of well-known materials, processing techniques, components, and equipment are omitted so as not to unnecessarily obscure the invention in detail. It should be understood, however, that the detailed description and the specific examples, while indicating particular embodiments of the invention, are given by way of illustration only and not by way of limitation. Further, the illustrated figures are only exemplary and are not intended to assert or imply any limitation with regard to the environment, architecture, design, or process in which different embodiments may be implemented. Various substitutions, modifications, additions, and/or rearrangements within the spirit and/or scope of the underlying inventive concept will become apparent to those skilled in the art from this disclosure.

Other features and advantages of the disclosed embodiments will be or will become apparent to one of ordinary skill in the art upon examination of the following figures and detailed description. It is intended that all such additional features and advantages be included within the scope of the disclosed embodiments.

As used within the written disclosure and in the claims, the terms "including" and "comprising" are used in an open-ended fashion, and thus should be interpreted to mean "including, but not limited to". Unless otherwise indicated, as used throughout this document, "or" does not require mutual exclusivity. In addition, as used herein, the singular forms "a", "an" and "the" are intended to include the plural forms as well, unless the context clearly indicates otherwise.

The disclosed embodiments include systems, methods, and computer program products for performing a calorie optimization respiratory exchange (CORE) metabolic determination and generating an individualized metabolic profile for each user. In some embodiments, the CORE system is also configured to determine an individualized exercise heart rate profile as a percentage of maximum heart rate from the metabolic profile and/or determining for the user a unique nutritional guideline from the metabolic profile.

The disclosed embodiments are based on the analysis of respiratory exchange tests performed on individuals of varied adult ages, socioeconomic backgrounds, general health status, and fitness over the course of many years. The results of the tests were compiled and regressively analyzed to determine a statistically significant mathematical model of an individual's fat and carbohydrate metabolism.

As an example, FIG. 1 is a graph of a mathematical model depicting substrate utilization (kcal/min vs. heart rate) corresponding to five critical points associated with fat and carbohydrate metabolism in accordance with an embodiment. In the depicted embodiment, the x-axis 110 represents heart rate (beats/minute) and the y-axis 112 represents fat metabolism (Kcal/minute). Curve 101 represents fat metabolism versus heart. Curve 102 represents carbohydrate metabolism versus heart.

In one embodiment, using the mathematical model that represents substrate utilization (kcal/min vs. heart rate), five critical points, a resting fat point 1, an energy of daily living point 2, a peak fat point 3, a metabolic equivalency point 4, and a carbohydrate dependency point 5 that are associated with fat and carbohydrate metabolism are determined. In one embodiment, the resting fat point 1 is equal to 22.23% of the energy of daily living point 2. In one embodiment, the target exercise heart rate zone is determined to be between the peak fat point 3 and the metabolic equivalency point 4 as indicated in FIG. 1.

In one embodiment, further analysis required evaluating the biometric variables of the tested individuals and quantifying the relative significance of each of these variables, for each of the five points, of their metabolic curves. For example, in one embodiment, the following variable relative weights are assigned to each of the points:

Points 1 and 2 (fat usage): 80% nutrition, 10% age, 10% exercise volume.

Point 3 (fat usage): 40% nutrition, 20% age, 20% exercise volume, 20% exercise intensity.

Point 3 (% heart rate maximum): 40% age, 30% exercise volume, 30% exercise intensity.

Point 5 (% heart rate maximum): 60% exercise intensity, 20% age, 20% exercise volume.

In one embodiment, the CORE system accounts for user's biometric data in a user profile. For example, in one embodiment, the biometric data of a user include age (years), height (centimeters or inches), weight (kilograms, pounds, or stone pounds), diet, and fitness of the individuals.

In addition, in one embodiment, a unique nutrition scale for the determination of nutrition status is developed. An example of a nutrition scale is illustrated in FIG. 4. In one embodiment, the nutrition scale is dependent upon the percentage of fat in an individual's diet (the % dietary fat can be entered by the user from an outside source of information that they may possess, or estimated via a number of developed dietary queries). The scale for fitness status (exercise intensity: FIG. 5 and exercise volume: FIG. 6) utilized queries from a widely disseminated description of exercise intensity and volume and we modified the weights of those queries to fit our model:

For example, in one embodiment, the following fitness scale is applied:

Little to no exercise: Intensity=1, Volume=1
20'3× per week: Intensity=3, Volume=2
60'4× per week: Intensity=5, Volume=3
60'7× per week: Intensity=8, Volume=4
Intense: Intensity=10, Volume=5

FIG. 2 is an example survey or questionnaire of the user queries for fitness and nutrition. An example of system biometrics and data is illustrated in FIGS. 3-7.

Based on the above analysis, the system is configured determined the proportional value of each of these variables relative to their metabolic contribution for each of the five points. In one embodiment, a widely disseminated formula (220−age) is used for the estimation of maximum heart rate. As stated above, the 5 critical metabolic points for fat and carbohydrate (kcals/min) vs. heart rate (beats/minute) are described as follows:

point (1) resting fat metabolism (RF),
point (2) energy of daily living (EDL),
point (3) peak fat metabolism (PF),
point (4) metabolic equivalency point (MEP), point (5) carbohydrate dependency (CD-zero fat burn).

Figure 8:
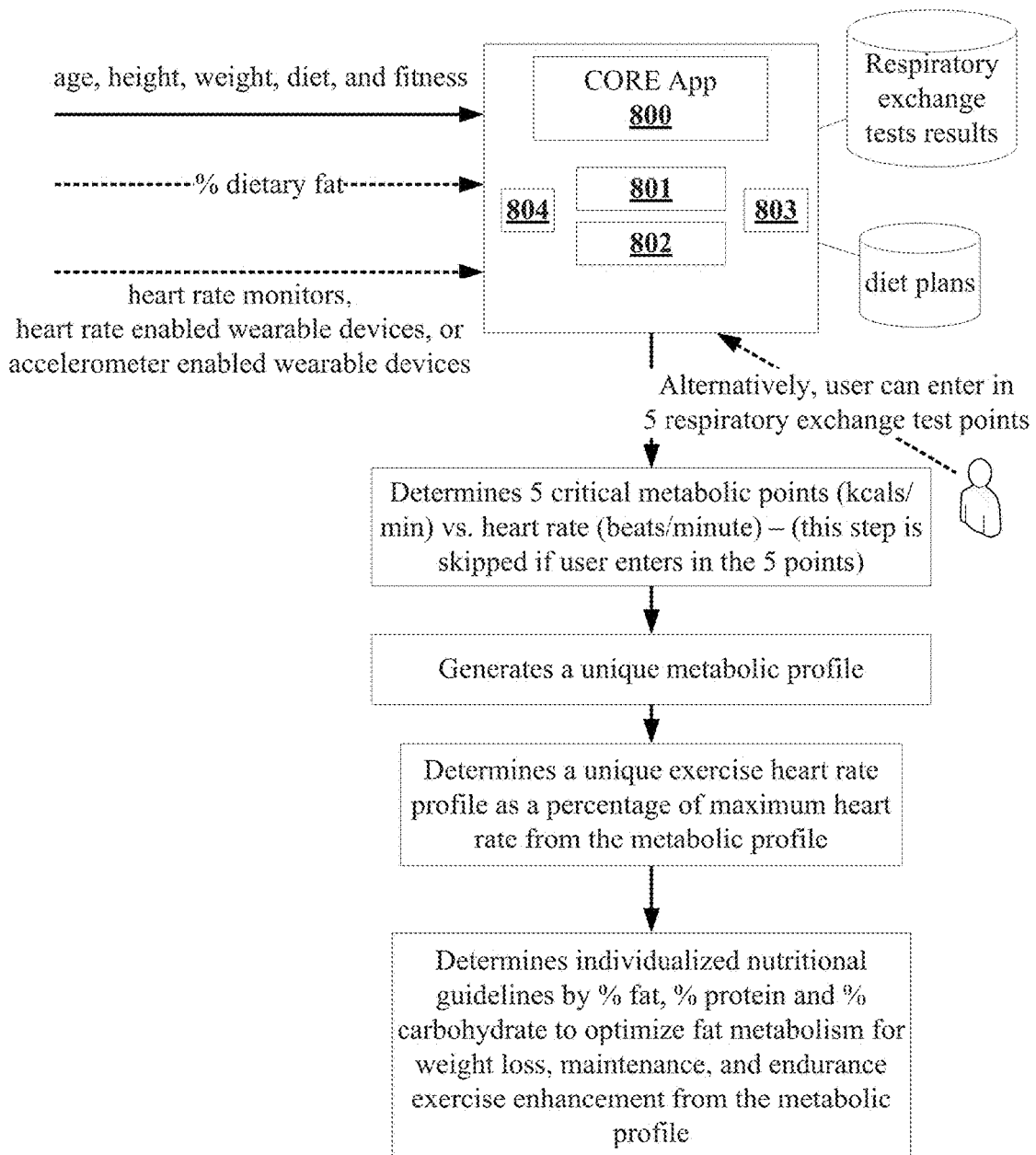
FIG. 8 is a high level block diagram illustrating a calorie optimization respiratory exchange metabolic system in accordance with one embodiment.

FIG. 8 is a high level block diagram illustrating an embodiment of a CORE application 800. As depicted in the example embodiment, the CORE application 800 may be implemented in a mobile application that is installed on a user device such as but not limited to a mobile device, a smart watch, laptop, tablet, or other computing device. Alternatively, the CORE application 800 may be implemented as a web application accessible to the user through the Internet or other communication networks. In this embodiment, the web application interface may be hosted by a Web server, whereas the computer executable instructions associated with the CORE application 800 may be executed on one or more backend servers. As understood by one of ordinary skill in the art, each of these computing devices contain memory 801 (volatile and/or non-volatile memory) and one or more processors 802 for storing and executing the instructions associated with the CORE system. In addition, each of these computing devices include a networking component or network interface 803 that enables the devices to communicate with other devices over a network such as, but not limited to, the Internet. The system executing the CORE application is referred to herein as the CORE system. In one environment, the CORE system communicates with one or more databases for retrieving respiratory exchange test results or dietary plan information. The CORE system also includes input/output interfaces 804 for receiving data such as user input data from one or more peripheral devices such as a keyboard, mouse, built-in buttons, heart rate monitor, and/or a touch screen display.

In one embodiment, the CORE system receives age, height, weight, diet, and fitness information for a particular user. In certain embodiments, the CORE system may also receive percentage of dietary fat information for the user. Still, in another embodiment, the CORE system is configured to enable a user to enter the data from outside respiratory exchange tests directly into the 5 points of the CORE system in order to generate their metabolic profile and access the additional functions.

Alternatively, in some embodiments, the CORE system is configured to receive data from heart rate monitors, heart rate enabled wearable devices, or accelerometer enabled wearable devices associated with the user. For example, while not necessary for minimal functional use, the CORE metabolic profile provides exceptional utility and value when used in conjunction with heart rate monitors, heart rate enabled wearable devices, or accelerometer enabled wearable devices that estimate kilocalorie expenditure with activity, to convert daily kcal energy expenditure into fat and carbohydrate kcal expenditure. With certain wearable heart rate enabled devices this may be a real-time measurement (fat and carbohydrate kcal/minute), with others a conversion of daily kcal values.

In accordance with one embodiment, the CORE system determines the above 5 points and then generates an individualized metabolic profile for each user. In another embodiment, a user enters specific data for points 1 through 5 as determined directly by previous respiratory exchange testing in order to generate their metabolic profile.

The CORE system then determines an individualized exercise heart rate profile (ranging from point 3 to point 4) for each user, as a percentage of maximum heart rate, from the CORE metabolic profile, to illustrate optimal target heart rate zone for peak fat metabolism (FIG. 1). The profile may be combined with calorie restriction weight loss programs based upon basal metabolic rate and total estimated energy requirements to determine and monitor resting, energy of daily living, and exercise fat metabolism for optimal nutrition planning.

The CORE system metabolic outcomes are used to determine individualized nutritional guidelines of % fat, % protein and % carbohydrate (FIG. 7) to optimize fat metabolism for weight loss, maintenance, and maximizing endurance exercise performance. FIG. 9 provides an example of nutritional requirements or diet plan for meeting the determined individualized nutritional guidelines. In one embodiment, the CORE system subsequently updates the database of thousands of macronutrients with customized and progressively modified diet plans consistent with metabolic changes over time.

FIG. 10 illustrates an example algorithm or process 1000 executed by the calorie optimization respiratory exchange metabolic system in accordance with one embodiment. The process begins at step 1002 by receiving user profile data. As described above, the profile data may be received through the user input or directly by communicating with one or more devices or systems. In one embodiment, the user profile data includes age, height, weight, nutrition status value (see FIG. 4), exercise intensity value (see FIG. 5), and/or exercise volume value (see FIG. 6). In some embodiments, the process may be configured to optionally receive the 5 points of data from a personal respiratory exchange test.

At step 1004, the process is configured to determine the Core Metabolic System functions including determining the maximum heart rate, resting metabolic rate, nutrition status, metabolic points, target fat metabolism exercise zone, macronutrient profile for future diet guideline, daily estimated energy expenditure, and daily estimated total energy expenditure. As an example, in one embodiment, the process performs the following calculations:

Calculate maximum heart rate: 220−age

Calculate Resting Metabolic Rate (RMR): Mifflin−St. Jeor model (kcal/day)

Male: 9.99×weight (kg)+6.25×height (cm)−4.92×age (yrs.)+5

Female: 9.99×weight (kg)+6.25×height (cm)−4.92×age (yrs.)−161

Calculate nutrition status if no fat % value entered by user (FIG. 4)

Calculate Metabolic Points 1-5: Refer to FIGS. 3 (Age), 4 (Nutrition Value), 6 (Exercise Volume Value), 5 (Exercise Intensity Value), and ## (Weight Coefficient)

Point 1 (Resting Fat (RF) kcal/min): Point 2×22.23%

Point 2 (Energy of Daily Living (EDL) Fat kcal/min):
((Nutrition value×80%)+(Age×10%)+(Exercise volume value×10%))

Point 3 (Peak Fat (PF) kcal/min):
((Nutrition value×40%)+(Age×20%)+(Exercise volume value×20%)+(Exercise intensity value×20%))

Point 3 (% maximum heart rate−beats/minute):
((Age×40%)+(Exercise volume value×30%)+(Exercise intensity value×30%))

Point 4 (Mean Equivalency point (MEP)−% maximum heart rate−beats/minute):
((Nutrition value×30%)+(Age×10%)+(Exercise volume value×30%)+(Exercise intensity value×30%))

Point 5 (Carbohydrate dependency (CD)−% maximum heart rate−beats/minute):
((Age×20%)+(Exercise volume value×20%)+(Exercise intensity value×60%))

Calculate User Target Fat Metabolism (burn) Exercise Zone: (% maximum heart rate and BPM): Range from Point 3 to Point 4

Calculate Macronutrient profile for future diet guideline: FIG. 7

Calculate Daily Estimated Energy Expenditure (EEE):

Data comes from the system metabolic profiles and incorporates wearable heart rate data or step counts to recalculate kcal/min into fat and carbohydrate kcal/min for resting (point 1), energy of daily living (point 2), and exercise.

Calculate Daily Estimated Total Energy Expenditure (TEE):

Data comes from adding the RMR and EEE kcals/min

Formulates charts for calories burned (fat and carbohydrate utilization) for resting, energy of daily living, exercise and total by day, week and month.

Formulates charts for steps taken with energy of daily living, exercise and total by day, week and month An example calculation is shown below:

Example: 50 year old male, 177.8 cm, 64 kg

Maximum heart rate: 220−50=170

RMR: Mifflin-St. Jeor=1510 kcal/day

Point 1: 3.78 kcal/minute×22.23%=0.84 kcal/minute RF burn=1209.6 kcal/day of RF burn Point 2: ((3.9 kcal/min×80%)+(3.1 kcal/min×10%)+(3.5 kcal/min×10%))=3.78 kcal/minute EDL fat burn=226.8 kcal/hour of EDL fat burn Point 3: ((4.3×40%)+(3.9×20%)+(4.5×20%)+(4.4×20%))=4.28 kcal/min PF burn=256.8 kcal/hour PF burn Point 3: ((43×40%)+(47×30%)+(50×30%))=42.3% maximum heart rate=72 BPM for PF Point 4: ((42×30%)+(60×10%)+(70×30%)+(66×30%))=59.4% maximum heart rate=101 BPM for MEP Point 5: ((69×20%)+(84×20%)+(70×60%))=73.6% maximum heart rate=125 BPM for CD Target Fat Burn Exercise Zone: (42.3−59.4% and 72−101 BPM)

Macronutrient profile: Fat 40%/Protein 28%/Carbohydrate 32%

Referring back to FIG. 10, at step 1006, the process receives the user's goals and preferences. For example, in one embodiment, the process receives the user's weight loss goal (e.g., amount desired to lose and period of time) and food preferences and/or food allergy restrictions.

At step 1008, the process determines the amount of user calories to lose/day over the given period of time. At step 1010, the process identifies and presents nutrition options from the customized food database for the user to develop personalized diet based upon system nutrition percentages and user weight loss goals.

At step 1012, the process monitors and updates the user's progress based on the user's calorie intake and biometric changes. For example, in one embodiment, the process determines the amount of user daily calories in and out and charts the user's progress daily, weekly and monthly relative to goal. Additionally, in one embodiment, the process is configured to receive periodic updated biometric changes as prompted by system, or as needed. For example, in one embodiment, the process periodically updates user metabolic profile, heart rate profile, nutrition percentages and diet options.

As previously stated, the above description including the diagrams are intended merely as examples of the disclosed embodiments and is not intended to limit the structure, process, or implementation of the disclosed embodiments. As understood by one of ordinary skill in this art that certain aspects of the disclosed embodiments described herein may be implemented as firmware, firmware/software combination, firmware/hardware combination, or a hardware/firmware/software combination.

It is further understood that various modifications may be made therein and that the subject matter disclosed herein may be implemented in various forms and examples, and that the teachings may be applied in numerous applications, only some of which have been described herein. It is intended by the following claims to claim any and all applications, modifications, and variations that fall within the true scope of the present teachings.

We claim:

1. A calorie optimization respiratory exchange metabolic system comprising:
   a computer-readable storage media having stored thereon computer-executable instructions;
   at least one peripheral device for interfacing data between at least one of a biometric device and a touch screen;
   a processor for executing the computer-executable instructions, wherein the computer-executable instructions include instructions for:
      generating an input and output interface for interfacing data between the biometric device and the touch screen;
      receiving user profile data of a user, wherein the user profile data includes age, height, weight, diet, and fitness information;
      determining five metabolic points versus heart rate;
      generating an individualized metabolic profile for the user based on the five metabolic points;
      determining for the user an individualized nutritional guideline from the metabolic profile, wherein the individualized nutritional guideline is determined by percent fat, percent protein and percent carbohydrate to optimize fat metabolism for weight loss, maintenance, and endurance exercise enhancement; and
      determining an individualized exercise heart rate profile as a percentage of maximum heart rate from the metabolic profile;
      interfacing the individualized metabolic profile and the nutritional guideline over the touch screen interface;
      wherein determining the five metabolic points (kcals/min) versus heart rate (beats/minute) is in response to receiving the metabolic points as input from a respiratory exchange test database, the metabolic points determined from a respiratory exchange test;
      wherein the five metabolic points are a resting fat point, an energy of daily living point, a peak fat point, a metabolic equivalency point, and a carbohydrate dependency point.

2. A calorie optimization respiratory exchange metabolic system comprising:
   a computer-readable storage media having stored thereon computer-executable instructions;
   at least one peripheral device for interfacing data between at least one of a biometric device and a touch screen;
   a processor for executing the computer-executable instructions, wherein the computer-executable instructions include instructions for:
      generating an input and output interface for interfacing data between the biometric device and the touch screen;
      receiving user profile data of a user;
      determining metabolic points versus heart rate;
      generating an individualized metabolic profile for the user; and determining an individualized exercise heart rate profile as a percentage of maximum heart rate from the metabolic profile;

determining for the user an individualized nutritional guideline from the metabolic profile;

interfacing the individualized metabolic profile and the nutritional guideline over the touch screen interface;

wherein the user profile data includes age, height, weight, diet, and fitness information;

wherein determining the metabolic points (kcals/min) versus heart rate (beats/minute) is in response to receiving the metabolic points as input from a respiratory exchange test database, the metabolic points determined from a respiratory exchange test;

wherein there are five metabolic points;

wherein the five metabolic points are a resting fat point, an energy of daily living point, a peak fat point, a metabolic equivalency point, and a carbohydrate dependency point.

3. The calorie optimization respiratory exchange metabolic system of claim 2, wherein the individualized nutritional guideline is determined by percent fat, percent protein and percent carbohydrate to optimize fat metabolism for weight loss, maintenance, and endurance exercise enhancement.

4. The calorie optimization respiratory exchange metabolic system of claim 2, wherein the computer-executable instructions include instructions for generating a web-based user interface for receiving data from the user of the Internet.

5. The calorie optimization respiratory exchange metabolic system of claim 2, wherein the diet information includes an average percentage of daily fat intake.

6. The calorie optimization respiratory exchange metabolic system of claim 5, wherein the average percentage of daily fat intake has a default value of eighteen percent.

7. The calorie optimization respiratory exchange metabolic system of claim 2, wherein the fitness information includes a resting heart rate.

8. The calorie optimization respiratory exchange metabolic system of claim 2, wherein a target exercise heart rate zone is determined to be between a peak fat point and a metabolic equivalency point.

9. A computer-implemented method comprising:

generating an input and output interface for interfacing data between a biometric device and a touch screen device;

receiving user profile data of a user;

determining metabolic points versus heart rate;

generating an individualized metabolic profile for the user; and determining an individualized exercise heart rate profile as a percentage of maximum heart rate from the metabolic profile;

determining for the user an individualized nutritional guideline from the metabolic profile;

interfacing the individualized metabolic profile and the nutritional guideline over the touch screen device interface;

wherein the user profile data includes age, height, weight, diet, and fitness information;

wherein determining the metabolic points (kcals/min) versus heart rate (beats/minute) is in response to receiving the metabolic points as input from a respiratory exchange test database, the metabolic points determined from a respiratory exchange test;

wherein there are five metabolic points;

wherein the five metabolic points are a resting fat point, an energy of daily living point, a peak fat point, a metabolic equivalency point, and a carbohydrate dependency point.

10. The computer-implemented method of claim 9, wherein the individualized nutritional guideline is determined by percent fat, percent protein and percent carbohydrate to optimize fat metabolism for weight loss, maintenance, and endurance exercise enhancement.

11. The computer-implemented method of claim 9, further comprising generating a web-based user interface for receiving data from the user of the Internet.

* * * * *